US012688911B2

(12) United States Patent  
Culver et al.

(10) Patent No.: US 12,688,911 B2  
(45) Date of Patent: *Jul. 21, 2026

(54) SYSTEM FOR PROVIDING A DATA MARKET FOR HEALTH DATA AND FOR PROVIDING REWARDS TO DATA MARKET PARTICIPANTS

(71) Applicant: Humana Inc., Louisville, KY (US)

(72) Inventors: Kyle Culver, Coxs Creek, KY (US); Emily Braun, Louisville, KY (US); Rohit Wason, Louisville, KY (US); Nicholas Hill, Louisville, KY (US); Zachary A. Stout, Louisville, KY (US); Matthew A Plappert, Louisville, KY (US); Chulmin Lee, Prospect, KY (US); Benjamin Singer, Louisville, KY (US); Norman Leach, Jeffersonville, IN (US)

(73) Assignee: Humana Inc., Louisville, KY (US)

( * ) Notice: Subject to any disclaimer, the term of this patent is extended or adjusted under 35 U.S.C. 154(b) by 55 days.

This patent is subject to a terminal disclaimer.

(21) Appl. No.: 18/667,274

(22) Filed: May 17, 2024

(65) Prior Publication Data

US 2024/0304291 A1 Sep. 12, 2024

Related U.S. Application Data

(63) Continuation of application No. 17/073,851, filed on Oct. 19, 2020, now Pat. No. 11,990,215, which is a  
(Continued)

(51) Int. Cl.  
*G16H 10/60* (2018.01)  
*G06F 9/54* (2006.01)  
(Continued)

(52) U.S. Cl.  
CPC ............. *G16H 10/60* (2018.01); *G06F 9/547* (2013.01); *G06F 16/27* (2019.01); *G06F 21/645* (2013.01);  
(Continued)

(58) Field of Classification Search  
CPC ........ G16H 10/60; G16H 15/00; G16H 80/00; G06F 9/547; G06F 16/27; G06F 21/645;  
(Continued)

(56) References Cited

U.S. PATENT DOCUMENTS 9,397,985 B1 * 7/2016 Seger, II ............. H04L 63/0442  
9,825,931 B2 11/2017 Johnsrud et al.  
(Continued)

OTHER PUBLICATIONS

Polina Mamoshina et al., Converging Blockchain and Next-Generation Artificial Intelligence Technologies to Decentralize and Accelerate Biomedical Research and Healthcare, Nov. 9, 2017, Oncotarget, pp. 5665-5690 (Year: 2017).*  
(Continued)

*Primary Examiner* — Nilesh B Khatri  
(74) *Attorney, Agent, or Firm* — Standley Law Group LLP; Jeffrey S. Standley; Adam J. Smith

(57) ABSTRACT

A system for maintaining accurate health data and for providing rewards to data market participants. A marketplace platform based on Blockchain technology leverages smart contracts to provide rewards to sellers of data assets that provide corrections or updates to medical data, such as provider demographics. A URL API is provided to a buyer of the data with an encrypted password that is used to access the data from the URL API.

13 Claims, 12 Drawing Sheets

Related U.S. Application Data continuation of application No. 15/883,987, filed on Jan. 30, 2018, now Pat. No. 11,942,195.

(51) Int. Cl.

| | |
|---|---|
| *G06F 16/27* | (2019.01) |
| *G06F 21/64* | (2013.01) |
| *G06Q 20/38* | (2012.01) |
| *G06Q 30/0207* | (2023.01) |
| *G16H 15/00* | (2018.01) |
| *G16H 80/00* | (2018.01) |
| *H04L 9/32* | (2006.01) |

(52) U.S. Cl.
CPC ..... *G06Q 20/3829* (2013.01); *G06Q 30/0207* (2013.01); *G16H 15/00* (2018.01); *G16H 80/00* (2018.01); *H04L 9/3247* (2013.01)

(58) Field of Classification Search
CPC ............ G06Q 20/3829; G06Q 30/0207; H04L 9/3247
See application file for complete search history.

(56) References Cited

U.S. PATENT DOCUMENTS

| | | | |
|---|---|---|---|
| 10,826,875 | B1 * | 11/2020 | Kim .................... H04L 63/0428 |
| 2001/0047322 | A1 | 11/2001 | Plate et al. |
| 2002/0073049 | A1 | 6/2002 | Dutta |
| 2002/0087461 | A1 | 7/2002 | Ganesan et al. |
| 2005/0005168 | A1 * | 1/2005 | Dick .................... G06F 16/217 |
| | | | 707/999.009 |
| 2005/0021781 | A1 * | 1/2005 | Sunder ................. H04W 12/06 |
| | | | 709/229 |
| 2005/0251473 | A1 | 11/2005 | Viviani |
| 2009/0210312 | A1 | 8/2009 | Frey et al. |
| 2010/0174727 | A1 * | 7/2010 | Zappacosta .......... G06F 16/951 |
| | | | 707/E17.14 |
| 2011/0196784 | A1 | 8/2011 | Newman et al. |
| 2012/0005071 | A1 | 1/2012 | Erbey et al. |
| 2012/0011034 | A1 * | 1/2012 | Thomas ............. G06Q 30/0641 |
| | | | 705/27.2 |
| 2012/0017266 | A1 | 1/2012 | DiChiara et al. |
| 2012/0144201 | A1 | 6/2012 | Anantha et al. |
| 2013/0297510 | A1 | 11/2013 | Ducote |
| 2014/0047513 | A1 | 2/2014 | van 't Noordende |
| 2014/0089027 | A1 | 3/2014 | Brown |
| 2015/0332283 | A1 | 11/2015 | Witchey |
| 2015/0370977 | A1 | 12/2015 | Weiss |
| 2015/0379510 | A1 * | 12/2015 | Smith ..................... G06F 21/64 |
| | | | 705/71 |
| 2016/0260171 | A1 | 9/2016 | Ford et al. |
| 2016/0328713 | A1 | 11/2016 | Ebrahimi |
| 2017/0039330 | A1 * | 2/2017 | Tanner, Jr. .......... G06Q 20/065 |
| 2017/0251025 | A1 | 8/2017 | Varley et al. |
| 2017/0337625 | A1 | 11/2017 | Rosenblatt et al. |
| 2018/0117446 | A1 | 5/2018 | Tran et al. |
| 2018/0218176 | A1 | 8/2018 | Voorhees et al. |
| 2019/0050868 | A1 * | 2/2019 | Shukla ............... G06Q 20/4016 |
| 2019/0109702 | A1 | 4/2019 | Maggu et al. |
| 2019/0205547 | A1 * | 7/2019 | Horvath ............. G06Q 20/3674 |
| 2019/0392928 | A1 * | 12/2019 | Hosseini ................ G16H 40/20 |

OTHER PUBLICATIONS

Andreas M. Antonopoulos, Mastering Bitcoin Unlocking Digital Crypto-Currencies, Dec. 2014, O'Reilly Media, Inc., 282 pages, 2014.

* cited by examiner

My Provider Directory     Dashboard   Records   Settings      Account balance: $832 | Welcome, Huma Search by NPI or name NPI   Sort by   Rec. Action

3829664322    BUY
Henderson, Michael

1234631445    BUY
Schmo, John

9604750622    BUY
Colbert, Lisa

2238953054    BUY
James, Edwin

6923547890    VERIFY
Smith, Nancy

3247952368    VERIFY
Billy, Bob

NPI: 3829664322      Record Value: High

| Hash | Provider | Verify date | Source | Owner |
|---|---|---|---|---|
| ...h4j9K4 | Henderson, Michael | 10/19/2018 | Purchased from market | Humana (You) |
| ...l33t3r | Henderson, Michael | 12/8/2018 | Direct outreach | Anthem | RECOMMENDED BUY ⓘ | Buy Record |
| ...h4j9K4 | Henderson, Michael | 10/19/2018 | Third party outreach | Optum + 17 more | Matches your record | Buy Record |
| ...9o044 | Henderson, Mike | 06/28/2017 | Third party outreach | Cigna + 4 more | | Buy Record |
| ...884fj0 | Henderson, Michael | 11/02/2017 | Direct outreach | Aetna + 3 more | | Buy Record |

FIG. 6

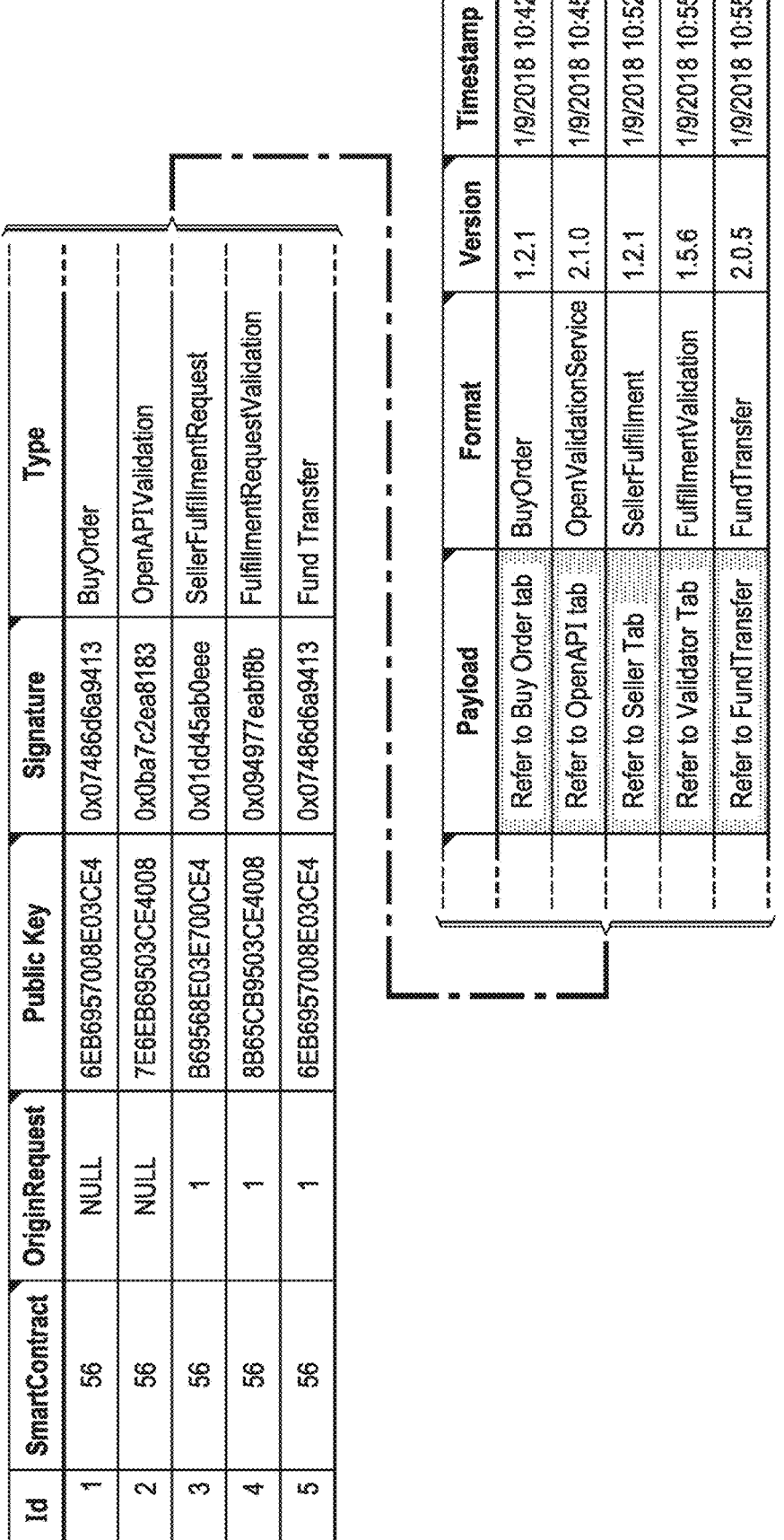

| Id | SmartContract | OriginRequest | Public Key | Signature | Type |
|----|---------------|---------------|------------|-----------|------|
| 1 | 56 | NULL | 6EB6957008E03CE4 | 0x07486d6a9413 | BuyOrder |
| 2 | 56 | NULL | 7E6EB69503CE4008 | 0x0ba7c2ea8183 | OpenAPIValidation |
| 3 | 56 | 1 | B69568E03E700CE4 | 0x01dd45ab0eee | SellerFulfillmentRequest |
| 4 | 56 | 1 | 8B65CB9503CE4008 | 0x094977eabf8b | FulfillmentRequestValidation |
| 5 | 56 | 1 | 6EB6957008E03CE4 | 0x07486d6a9413 | Fund Transfer |

| Payload | Format | Version | Timestamp |
|---------|--------|---------|-----------|
| Refer to Buy Order tab | BuyOrder | 1.2.1 | 1/9/2018 10:42 |
| Refer to OpenAPI tab | OpenValidationService | 2.1.0 | 1/9/2018 10:45 |
| Refer to Seller Tab | SellerFulfillment | 1.2.1 | 1/9/2018 10:52 |
| Refer to Validator Tab | FulfillmentValidation | 1.5.6 | 1/9/2018 10:55 |
| Refer to FundTransfer | FundTransfer | 2.0.5 | 1/9/2018 10:55 |

FIG. 7

| Field | Value |
|---|---|
| Transaction Id | 1 |
| Smart Contract Unique Identifier | 56 |
| Buyer's Public Key | 6EB6957008E03CE4 |
| Signature | 0x07486d6a9413e4a9aeddccf851ba7c2ea81835576b0afabbcfd62493ff0924ff400 27 d1dd45ab0eeee5803079086679a70d444a2d4ea7e8db221894977eabf8bfc |
| Identifier | 1234567890 |
| IdentifierType | NPI |
| PayloadHashOfExisting | 786A02F742015903C6C6FD852552D272912F4740E158476 18A86E217F71F5419 |
| AcceptedFulfillmentRequestTypes | Update to Truth, Data Quality Issue Notification, New Data Asset |
| Reward for Quality Issue Notification | 2 |
| Reward for Providing Data Asset | 5 |
| Validation Fee | 2 |
| Format of Data Asset | FHIR Practitioner Spec - https://www.hl7.org/fhir/practitioner.html |
| Format Type | JSON |
| Format Version | 3.0.1 |
| FormatValidationProcess | OpenApi |
| Timeliness | 5 Days |
| Source | Provider Attested |
| Seller Credibility Threshold (0-5 scale) | 4 |
| Acceptable Validators | Availity(PublicKey:008E036EB6957CE4), BetterDoctor(PublicKey: 3CE46EB6957008E0) |
| Expire Date Time | 12/31/2018 23:59 |

The rows from "Identifier" through "Expire Date Time" are grouped under the label Transaction Payload.

FIG. 8

| Field | Data |
|---|---|
| Transaction Id | 2 |
| Public Key | 6EB6957008E03CE4 |
| Signature | 0x0ba7c2ea81835576b0afabbcfd62493f7486d6a9413e4a9aeddccf851ff0924ff400 27 d1dd45ab0eeee58030790866679a70d444a2d4ea7e8db221894977eabf8bfc |
| DataOwner's Public Key | 9DC6957008E03BB4 |
| Data Owner's Signature | 0x081835576b7486d6a9413e4a9aeddccf851ba7c2ea0afabbcfd62493ff0924ff400 27 d1dd45ab0eeee58030790866679a70d444a2d4ea7e8db221894977eabf8bfc |
| Identifier | 1234567890 |
| IdentifierType | NPI |
| PayloadHash | A86E217F71F5419786A02F742015903C6C6FD852552D272912F4740E15847618 |
| Format of Data Asset | FHIR Practitioner. Spec - https://www.hl7.org/fhir/practitioner.html |
| Format Type | JSON |
| Format Version | 3.0.1 |
| FormatValidationProcess | OpenApi |
| IsValidated | TRUE |

Transaction Payload *(label spanning the rows from DataOwner's Public Key through IsValidated)*

FIG. 9

| Field | Value |
|---|---|
| Transaction Id | 3 |
| SmartContractId | 56 |
| PublicKey | 68E03EB69570OCE4 |
| Record Type | SellerFulfillmentRequest |
| AddressForSellerPayment | 6b53LETtpyT1BoatSLRHtKNngkdXEeobR7 |
| Identifier | 1234567890 |
| IdentifierType | NPI |
| PayloadHash | F4740E15847618A86E217F71F5419786A02F742015903C6C 6FD852552D272912 |
| FormatValidationResult | 2 |
| FulfillmentRequestType | Update to Truth |
| ContainsPHI | N |
| ContainsPI | N |
| ContainsPCI | N |
| API Url | www.sellersdata.com/provider/1234567890 |
| Validator Secret | 1912308409123890 |
| Buyer API Secret | 8409123890191230 |
| ExpireTime | 1/9/2019 12:00 |
| Signature | 0x027d1dd45ab0eeee58030790866679a70d444a2d4ea7e8 db221894977eabf8bfc7486d6a9413e4a9aeddccf851ba7c2 ea81835576b0afabbcfd62493ff0924ff400 |

Transaction Payload

FIG. 10

| Field | | Value |
|---|---|---|
| Transaction Id | | 4 |
| SmartContractId | | 56 |
| PublicKey | | 68E03EB695700CE4 |
| Record Type | | FulfillmentRequestValidation |
| Transaction Payload | AddressForValidatorPayment | SLRHtKNngkdXEeobR76b53LETtpyT1Boat |
| | TransactionValidated | 3 |
| | PayloadHash | F4740E15847618A86E217F71F5419786A02F742015903C6C6FD852552D272912 |
| | IsValidated | TRUE |
| Signature | | 0x094977eabf8bfc27d1dd45ab0eeee58030790866679a70d4444a2d4ea7e8db221 894977eabf8bfc7486d6a9413e4a9aeddccf851ba7c2ea81835576b0afabbcfd62 493f0924f400 |

FIG. 11

| | Field | Value |
|---|---|---|
| | Transaction Id | 5 |
| | SmartContractId | 56 |
| | PublicKey | 68E03EB695700CE4 |
| | Record Type | FulfillmentRequestValidation |
| | SourceOfFunds | gkdXEeobR76b53LETpyT1BoatSLRHtKNn |
| | ValidatorFee | 2 |
| | ValidatorAddress | SLRHtKNngkdXEeobR76b53LETpyT1Boat |
| Transaction Payload | SellerFee | 5 |
| | SellerAddress | 6b53LETpyT1BoatSLRHtKNngkdXEeobR7 |
| | SourceBalance | 1000 |
| | BalanceAddress | gkdXEeobR76b53LETpyT1BoatSLRHtKNn |
| | Signature | 0x0444a2d4ea7e8db2218949 77eabf8bfc7486d6a94977eabf8bfc27d1dd45ab0 eeee580307980866 79a70d9413e4a9aeddccf851ba7c2ea81835576b0afabbcfd62 493f0924ff400 |

FIG. 12

SYSTEM FOR PROVIDING A DATA MARKET FOR HEALTH DATA AND FOR PROVIDING REWARDS TO DATA MARKET PARTICIPANTS

CROSS-REFERENCE TO RELATED APPLICATION

This application is a continuation of non-provisional application Ser. No. 17/073,851 filed Oct. 19, 2020, which is a continuation of non-provisional application Ser. No. 15/883,987, filed Jan. 30, 2018, the disclosures of which is hereby incorporated by reference in its entirety as if fully recited herein.

BACKGROUND OF THE INVENTIVE FIELD

The present invention is directed to a system for maintaining accurate health data by connecting buyers and sellers of data and offering the capabilities needed to participate in a distributed data market. Enabling the efficient exchange of data is critical to improving health care. Information equips both physicians and patients to make decisions that impact their well-being. There is a need for a shared foundation or platform for the secure and efficient exchange of health information to decrease costs, improve efficiencies, and facilitate competition. In one embodiment of the invention, a Provider Directory Management (PDM) process is demonstrated to show how the shared foundation can facilitate the efficient and secure exchange of data.

This shared foundation acts a utility and serves as a data market for the entire industry. By acting as a market, and providing a platform for users, the sources of data represent "sellers" and the consumers of data "buyers". Structuring the foundation this way allows free market forces to act upon the current interoperability problems that plague the health care industry. Buyers can now utilize the market to incentivize sellers' behavior to improve data quality. For example, the buyer will pay more for data that is more current, or only pay for data that meets the formatting requirements that they have outlined in the contract. Sellers can now compete for the rewards of providing high quality data.

In one scenario, a physician is willing to pay a small fee for the medication claim history for a patient with a complicated list of medications. This request for data on the market would create competition across pharmacies, payers and other firms to fulfill this request and realize the reward.

In one embodiment, Blockchain technologies will power the shared platform and allow applications to compete while removing the high barriers to data access. This platform will benefit from the use of an established technology that provides a transparent and trusted foundation that reduces the friction in data exchange and uses the Blockchain—not only for the shared ledger, but also as the industry's "card catalog" system.

One of the first questions a health plan member asks when engaging with their health insurance is if their doctor is in network. Maintaining an accurate directory of providers with demographics is important to customer service. Because the provider details change rapidly, Provider Directory Management (PDM) is a necessary and ongoing set of processes for data maintenance. These processes cost millions of dollars per year and are currently very inefficient. Because customers and patients rely on directories to locate an in-network provider, these directories need to be maintained with accurate data.

The financial obligations of maintaining a national provider directory are significant. Approximately 162 MAOs maintain directories with similar levels of relative inefficiency and expense. The duplication is expensive and wasteful and is one of the problems solved by the present invention. Currently, each MA organization is spending millions curating a public provider data set and then isolating all that valuable data in their own silos.

There are several issues that contribute to industry inefficiencies in providing up-to-date provider directories, but the most significant is the frequency of change of provider data. Currently, most proposed updates are validated by manual processes including faxes, phone calls and word of mouth conversations that can take significant time to complete.

Providers maintain their practice information by updating each directory maintained by each payer and MAO. Physicians making updates must visit each Web portal or fax each update directly, which creates a "door-to-door" process. A provider's inability to broadcast updates to all the individual PDM data silos creates significant friction and inefficiency. Payers attempt to overcome this friction, and stay compliant with regulation, by reaching out to the providers to request updates. From a provider's perspective, this outreach creates a flood of faxes, emails and calls from all of the payers which whom they are affiliated, each attempting to obtain updated information. Because information is requested periodically, this onerous process contributes to an ongoing friction with providers. When asked directly about the situation, providers understandably exhibit little awareness about the needs of updating physician directories for a payer.

The present invention provides a shared mechanism to broadcast physician directory demographics that provides significant benefits. From an MAO perspective, the burden of building and maintaining a national scale directory is shared by the firms interested in collaborating that have a vested interest in accurate data. From a provider's perspective, the prospect of simplifying their process to a single update for all partners is significantly more efficient and reduces calls, faxes and emails. In one embodiment of the invention, the system is comprised of a crowd sourced Blockchain solution that provides a utility that is trusted, incentivized, and extensible for all players in the ecosystem. The present invention provides a platform that enables firms like MAOs to collaborate and crowd source provider directory data. The present invention enables incentives to reward crowd sourcing activities.

SUMMARY OF THE GENERAL INVENTIVE CONCEPT

In one embodiment of the invention, the system is configured for storing and updating up-to-date medical data and for providing reward incentives to systems users, the system comprising:

a first non-transitory computer readable medium with a first computer-readable program code stored thereon;

a first communication device;

a first processing device operatively coupled to the first non-transitory computer readable medium, wherein the first processing device is configured to execute a shared computer-readable program code (Buyer's smart contract) to:

provide a first executable portion of code for storage on a distributed ledger stored on a Blockchain distributed network, wherein the first executable portion of code is configured to:

store a public key of a first user (Buyer);

Optionally store a one way cryptographic hash of the data asset (Representation of Buyer's current data asset if applicable);

store the data asset requirements (including but not limited to formatting details, identifier, minimum seller creditability score, and timeliness)

store the reward value for providing the requested data asset that meets the requirements;

provide a cryptographic signature of the first portion of stored values using the first users public key to demonstrate authorship of the request wherein first computer-readable program code (off Block-chain code) is configured to:

receive an encrypted value (encrypted access key) encrypted using the public key of the first user (buyer);

decrypt the encrypted value (decrypted access key);

access a data resource using the decrypted value as an access key (connect to web service using decrypted access key);

receive a data asset at a specified location (receive data asset as web service response to URL provided by Seller);

validate the data asset meets the requirements set forth (check data asset meets requirements and Seller should be paid).

a second non-transitory computer readable medium using a shared computer-readable program code stored thereon;

a second communication device;

a second processing device operatively coupled to the second non-transitory computer readable medium, wherein the second processing device is configured to execute the first computer-readable program code (buyer's smart contract) to allow a second user (seller) to:

provide an address for the first user to send funds (Sellers Address);

provide an address where the second user has escrowed funds (Validation fee paid by seller should data not meet requirements)

provide location details (e.g., address) on where the data asset can be accessed (Web Service URL);

provide encrypted values using the public key of the first user (Buyer's Encrypted Access Key);

provide encrypted values using the public key of the validators (Validators' Encrypted Access Key);

provide a public key of the second user (Sellers Public Key);

provide identification information of the second user (Signature of Data Stored proving authorship of the information); and provide an updated hash of the stored data asset meeting the requirements;

wherein the second processing device is configured to execute the second computer-readable program code (off Blockchain Code) to:

authenticate the first user using decrypted value;

provide proposed data asset upon request by first user (Buyer;

provide one or more public keys for acceptable validators;

wherein the second processing device is configured to execute the second computer-readable program code to:

provide an encrypted value using the one or more public keys for acceptable validators;

wherein the encrypted value using the one or more public keys for acceptable validators is configured to be decrypted using at least one private key of at least one acceptable validator for use in accessing a data resource having the stored update to the medical data;

the system further comprising:

a third non-transitory computer readable medium with a third computer-readable program code stored thereon;

a third communication device;

a third processing device operatively coupled to the third non-transitory computer readable medium, wherein the third processing device is configured to execute the third computer-readable program code to:

receive the validation requirements;

receive the encrypted value using the one or more public keys for acceptable validators;

decrypt the encrypted value using at least one private key of at least one acceptable validator for use in accessing a data resource having the stored update to the medical data;

provide an indication that the update to the medical data is validated or is unfulfilled.

The foregoing and other features and advantages of the present invention will be apparent from the following more detailed description of the particular embodiments, as illustrated in the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 6 illustrates one embodiment of a graphical user interface of the present invention.

FIG. 7 illustrates one embodiment of a ledger for the present invention.

FIG. 8 illustrates one embodiment of a buy order block stored on the ledger of FIG. 7.

FIG. 9 illustrates one embodiment of an open API validation block stored on the ledger of FIG. 7.

FIG. 10 illustrates one embodiment of a seller fulfillment request block stored on the ledger of FIG. 7.

FIG. 11 illustrates one embodiment of a fulfilment request validation block stored on the ledger of FIG. 7.

FIG. 12 illustrates one embodiment of a fund transfer block stored on the ledger of FIG. 7.

DETAILED DESCRIPTION OF EXEMPLARY EMBODIMENT(S)

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

Figure 1:
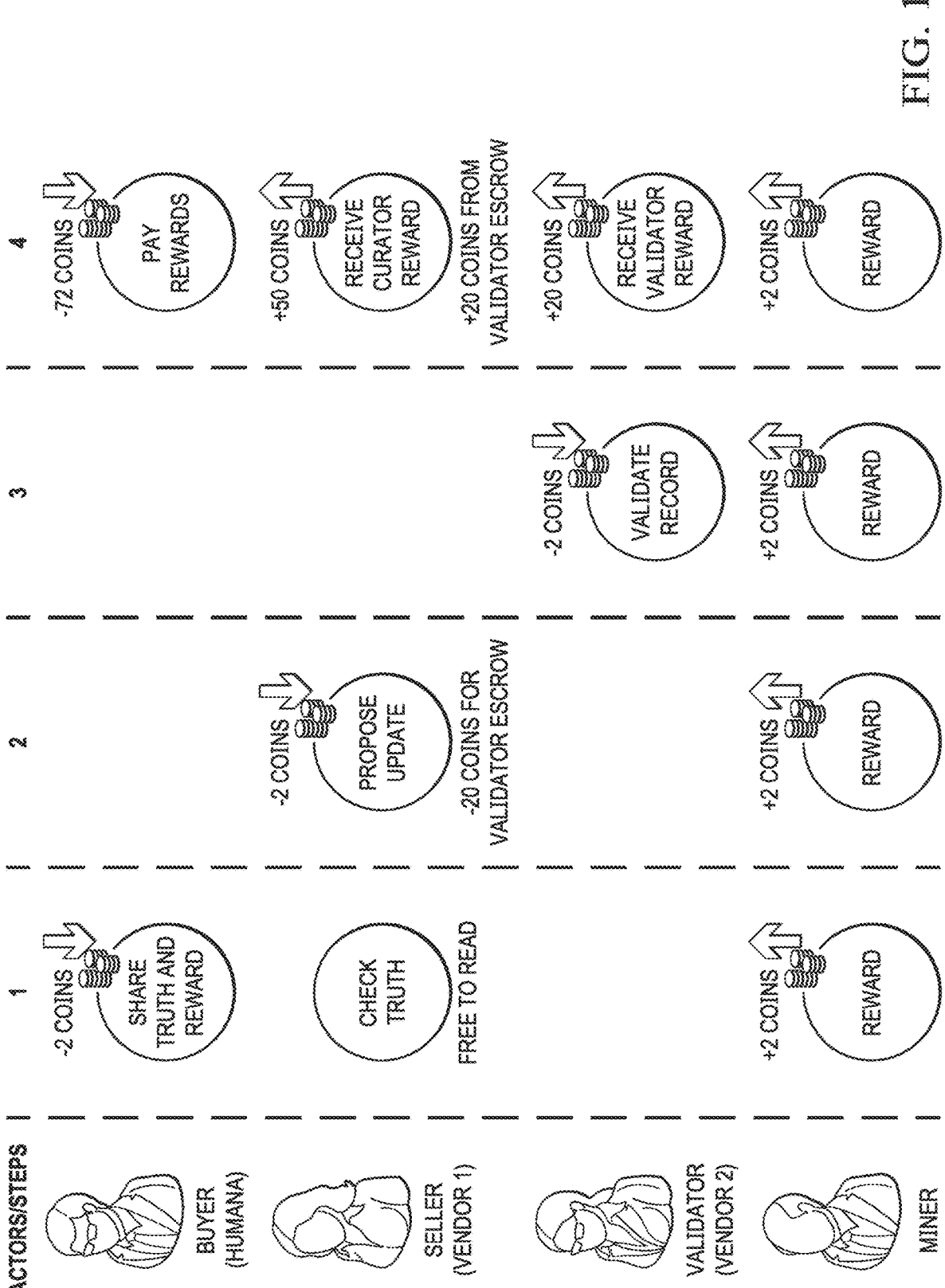
FIG. 1 illustrates one example of the transaction lifecycle on the marketplace platform of the present invention.
Figure 2:
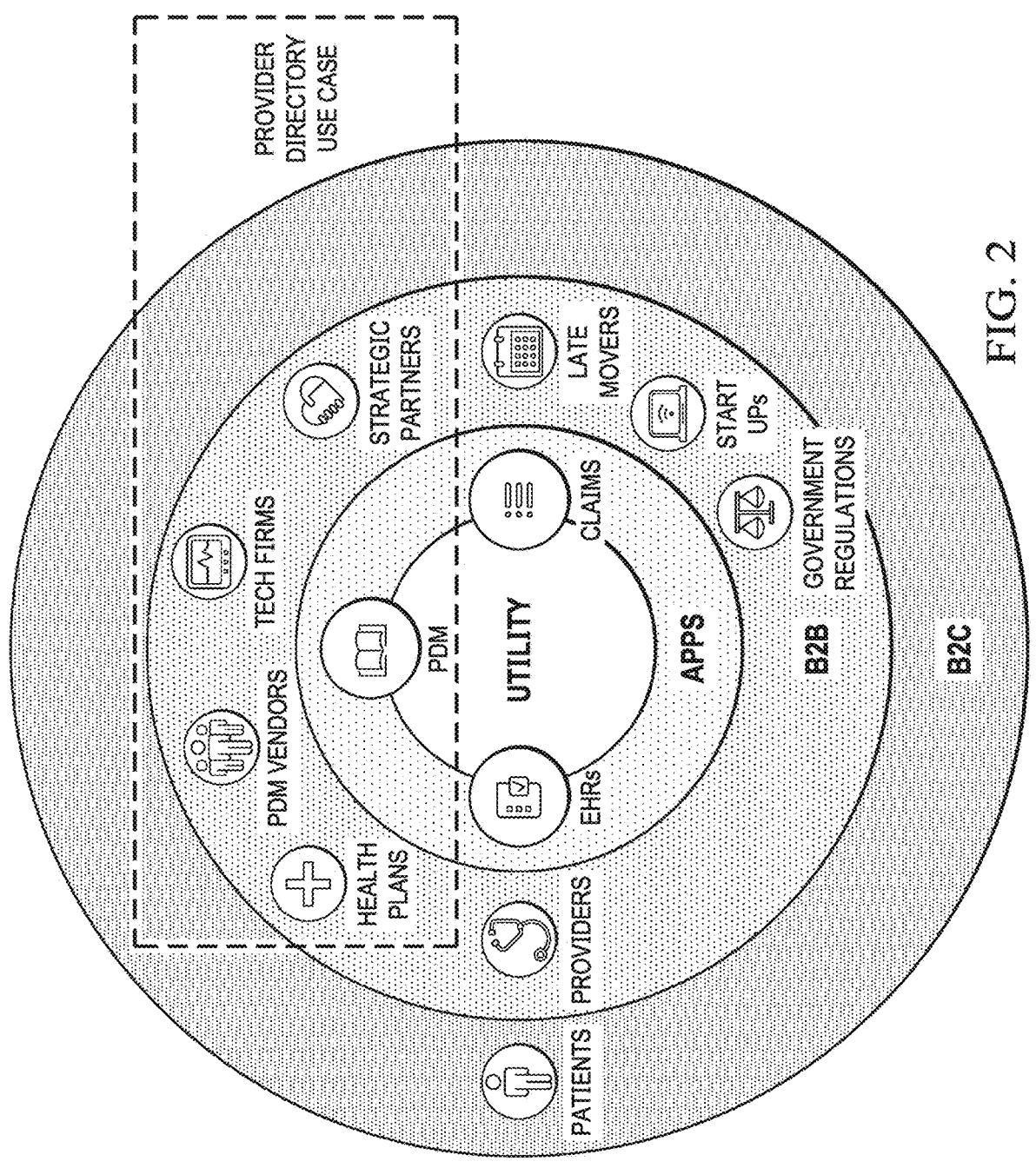
FIG. 2 illustrates a graphical view of the marketplace participants of the present invention.

FIG. 1 illustrates one example of the transaction lifecycle on the marketplace platform of the present invention. As illustrated, users of the marketplace platform of the present invention (e.g., buyers, sellers, validators of medical data), come together to provide updates to provider demographics. The system uses a Blockchain platform and smart contracts to provide rewards for sellers who identify data quality issues and who provide data updates, rewards to validators who review and verify the update, and rewards to miners for maintaining the infrastructure for the shared ledger.

Steps in a Successful Flow

1) Buyer (Humana) shares latest provider demographics (Truth) as well as a reward for A) the firm who finds an issue or suggests an update (Seller) and B) the firm who validates the proposed update. This information is shared with the network via "writing to the shared ledger" so there is a minimal cost paid to the miner for supporting the infrastructure.

2) Seller finds a data quality issue and proposes an update. This seller could be anyone seeking the reward however there is a cost to propose the update since it would require writing data to the shared ledger and again that cost would be paid to the miner. Also note the validation cost would be put into escrow and should the update be incorrect then that cost would be paid by the Seller.

3) Validator reviews the proposed update and decides if the record does require an update and then the reward is paid by the Buyer. This could be the Subscriber (Humana) or some set of trusted third parties looking to obtain the reward. Likely this would be automated as the process matured.

4) Buyer pays the Validator and the Seller for their contribution to the process. The Buyer then has an opportunity to share an updated provider demographics (Truth) as a new standing offer to restart the process for a future update when made available.

To realize the maximum benefit of a shared platform it functions as an industry utility. This allows for the drastic reduction in duplication caused by competing foundations. In one embodiment, the market system of the present invention is split into two parts: 1) a foundational Blockchain enabled utility; and 2) the applications that provide capabilities and experiences for users on top of that utility. The foundational utility is preferably built on Blockchain technologies to reduce friction and increase transparency. In one embodiment, this utility will be permissioned and private to limit risk while the system matures, however ensuring a low barrier of entry is a focal point of the utility to enable innovation and competition.

The present invention, facilitates the secure exchange of data assets and value. The applications built on top of the utility then compete by creating capabilities and experiences for the users that need to exchange information. For example, the capabilities and experience required to enable a user or system to crowd source provider directory data are built into the application which then integrates with the utility to exchange data assets. This exchange of data assets occurs on the Blockchain powered utility through smart contracts. Smart contracts enable buyers to publish a buy request and the market of sellers then compete to answer the request and realize the reward offered by the buyer. Free market forces are then enabled by buyers who can adjust pricing and sellers who compete to meet the buyer's needs.

Figure 3:
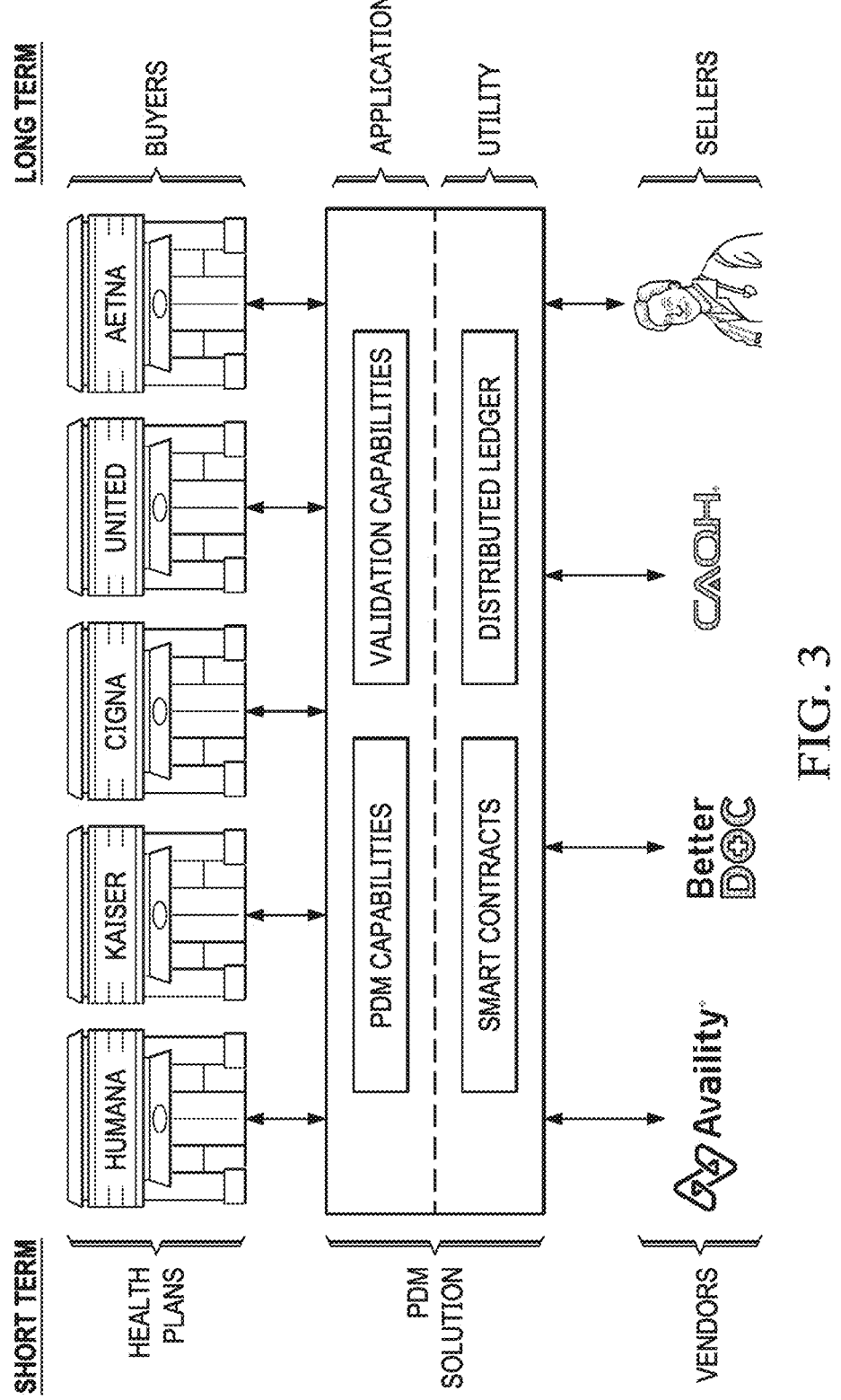
FIG. 3 illustrates a block diagram of the marketplace platform for a provider directory example.

Incentivizing the crowd to curate provider directory data creates a multisided market. FIG. 3 shows the market with the provider directory example of the present invention. MAOs on the top side of the market partner to share the burden of data maintenance while the lower side of the market competes for the rewards they offer. This gives the 160+ MAOs a mechanism to share costs for data they are mutually interested in and also dynamically adjust incentives to encourage the market of firms PDM capabilities to provide updates to the data. Duplication and cost is driven down for the MAOs and data collection improves because there is competition to realize the rewards offered.

Figure 4:
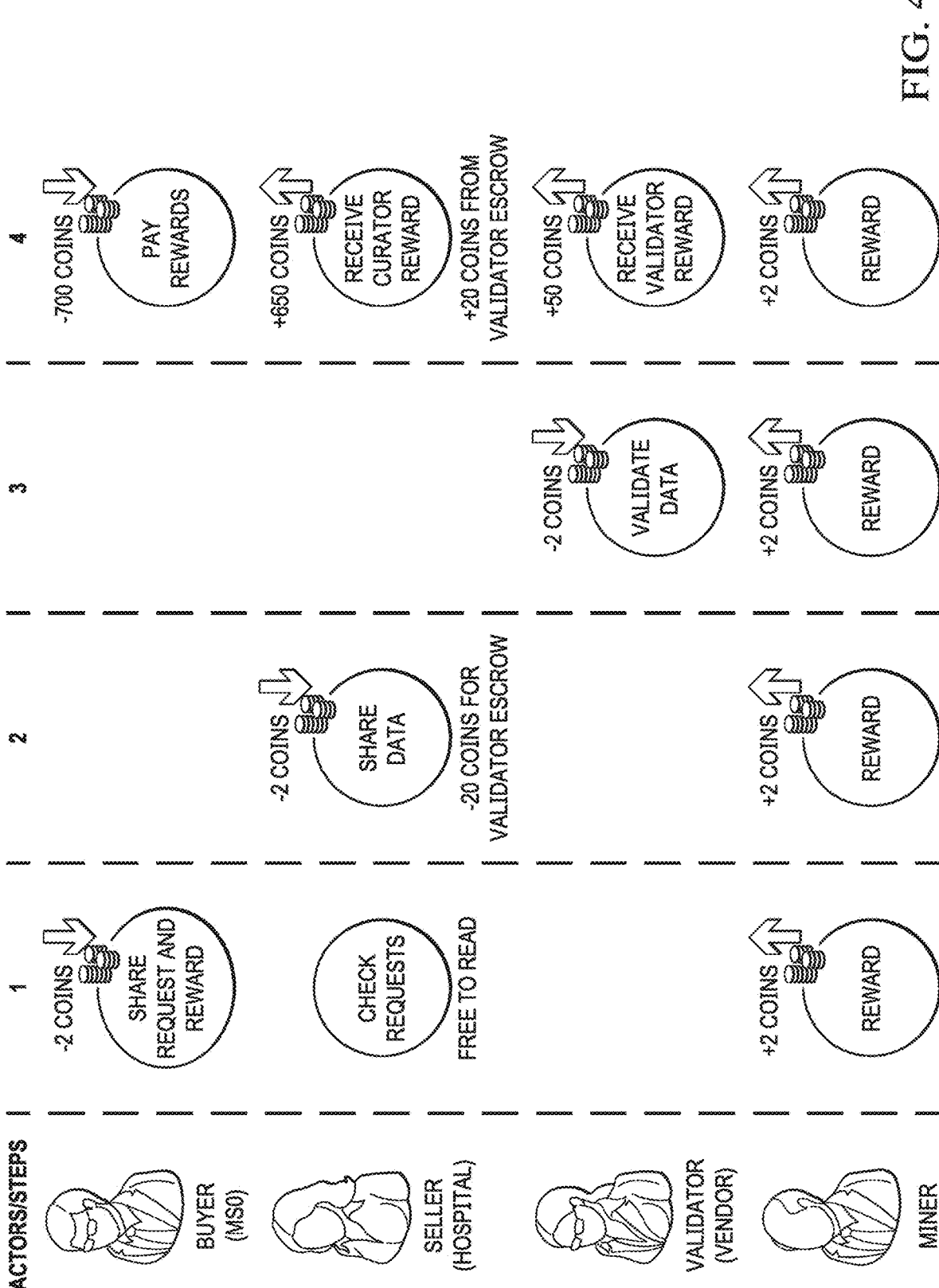
FIG. 4 illustrates the process flow for another example embodiment of the invention.

The examples discussed below illustrate the true potential of the distributed data market platform of the present invention. Quality measures like Medicare Risk Adjustment (MRA) and Healthcare Effectiveness Data and Information Set (HEDIS) revolve around patient information. This patient information is documented by the physician so that they are reimbursed for the care they are delivering. Given that there is a finite list of information that apply to MRA and HEDIS, a physician system could place standing buy requests for any information that impacts MRA and HEDIS measures for their patient. Should any other firm in the industry have applicable information, they could then exercise that standing buy request and fulfill the physician's query. The example process outlined in FIG. 4 adds context to this description.

For example, an entity (e.g., MSO, doctor or hospital) inputs a standing buy request for applicable medical information needed for a patient. A hospital sees the buy request and, having a diagnosis that meets the criteria, provides the diagnosis ("data update") to the system. The hospital receives a financial reward so that it is compensated for the update.

Steps in a Successful Flow

1) Buyer (MSO) shares a request for patient information that relates to the quality metric (MRA, HEDIS etc.) for their PCP client. For example, the request is if anyone has a diagnosis of CHF for Kyle. Given that this would impact MRA it has a value and ROI can be determined, thus a market created for that information at the record level.

2) Seller (Hospital) has information that meets the criteria of the request. For example, they have a FHIR compliant diagnosis message that states Kyle has CHF and it meets all the criteria outlined by the seller. Note these buyer requirements would drive behavior change because "bad data" would not be purchased. Data Quality and Interoperability could now be driven by very granular incentives.

3) Validator reviews data shared by the seller and checks it against the criteria outlined in the sellers request. The output of this validation would then be written to the shared ledger. Note this would mature toward automation and likely be something open that the seller could pre-check prior to sharing the data asset.

4) Buyer pays the Validator and the Seller for their contribution in the process and then utilizes the information shared to retrieve the data asset.

Figure 5:
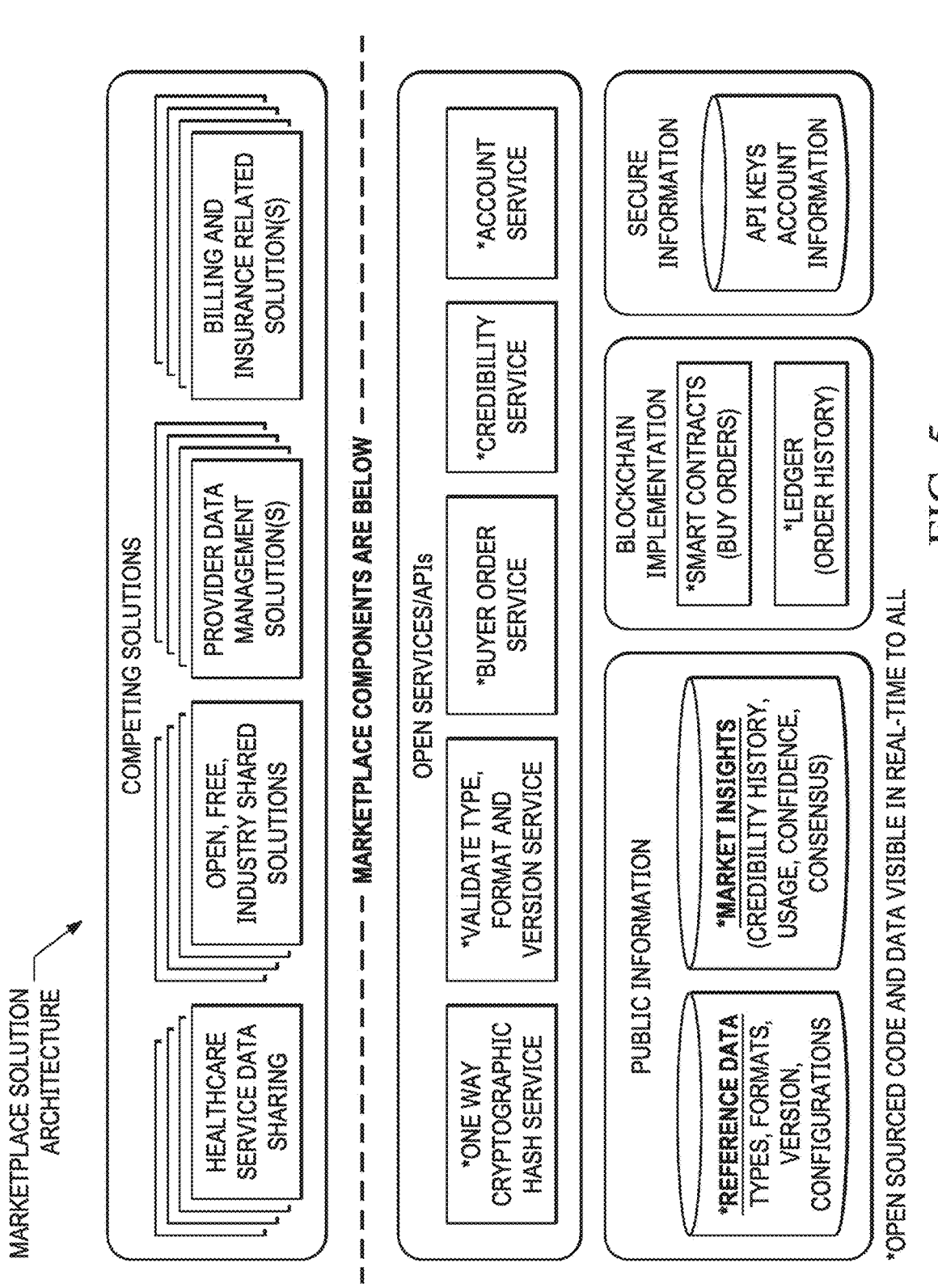
FIG. 5 illustrates a block diagram of a marketplace architecture of one embodiment of the present invention.

FIG. 5 illustrates a block diagram of a marketplace architecture of one embodiment of the present invention. As illustrated, open services, e.g., Application Programing Interfaces (APIs), are used by marketplace platform users (e.g., buyers, sellers, validators, miners) to input orders to buy data, to provide (seller) data updates to data assets, to provide validation of the updates. The transactions are stored on the ledger as blocks. In the preferred embodiment of the invention, the ledger is stored on a decentralized Blockchain platform. "Public Information" and "Secure Information"— can be separate data stores that separate from the transactional ledger. For example, the transaction ledger would store that Firm A bought Data Payload XYZ from Firm B. The payload itself would be stored in either Public Information or Secure Information Data storage solutions based on the requirements for that particular payload. To refer back to the card catalog analogy, the blocks for "Public" and "Secure" are shelves for the books and the ledger serves as the "library card catalog" that defines where things can be found (and tie them to the audit trail of the exchange/purchase transactions).

FIG. 6 illustrates one embodiment of a graphical user interface of the present invention for marketplace users to input buy orders, sell orders, and validation services. Buyers can see sellers' offerings, and once selected, it goes onto a queue for validators to work off of and validate the purchase.

Example process flow of one embodiment of the present invention: the process detailed below illustrates one example process of how buyers, sellers, validators and miners use the marketplace platform of the present invention to come together to keep provider information up-to-date on a decentralized, secure ledger using Blockchain technology as a base for the marketplace platform.

1) Buyer Makes Request for Data Asset on the Decentralized Distributed Data Marketplace:

Buyer System POSTS Data Asset to Open Services to get One Way Cryptographic Hash(Payload Hash).

Payload Hash persisted to BC, along with Source System.

Buyer System POSTS Data Asset to Open Services to Validate Type, Version and Format.

If Successful, Validation Result is persisted to BC along with Source & Payload Hash, Type, Version and Format.

Buyer System Creates Smart Contract on the Decentralized Distributed Data Marketplace for Purchase Request/Order containing:

Buyer Public Key(s);

Support Multiparty Buyers;

Address for Escrow of Validation funds;

Identification Information;

Value: e.g. 1234567890;

Type: NPI.

Payload Hash (optional).

Populated if you have a current "truth"

Blank if buyer has no knowledge and is asking for most recent data asset of this type.

Format Validation Result Transaction id (Optional).

Populated if current "truth" has been validated by Open APIs and result persisted to Public BC.

Reward for Finding Data Quality Issue.

$2.00 or 20 tokens.

Reward for Providing Data Asset (Which could be an Update to the proposed Truth).

$10.00 or 100 tokens.

Validation Requirements.

Format—FHIR Practitioner.

Type—Provider Record.

Format Validated by OpenApi.

Timeliness—Validated in past 24 hours.

Source.

Define the Source, etc., must come from Walgreens, CVS etc.

Seller Credibility Threshold.

Must have greater than X.

Acceptable Validators.

Public Keys for Third Parties that are trusted to validate.

Expire Date Time.

Note each write to the Blockchain would require a transaction fee and that fee would be paid to the infrastructure (miner) who was determined the leader by the consensus mechanism for the network at that point in time.

2) Seller Fulfills Data Asset Request:

Seller System Posts Data Asset to Open Services to get One Way Cryptographic Hash (Payload Hash).

Payload Hash persisted to BC, along with Source System.

Seller System Posts Data Asset to Open Services to Validate Type, Version and Format.

If Successful, Validation Result is persisted to BC along with Source & Payload Hash, Type, Version and Format.

Seller System Executes Smart Contract Purchase Fulfillment Order, writing the attempt to the Blockchain.

Seller Public Key.

Address for Buyer to Send Funds.

Identification Information.

Value: e.g. 1234567890.

Type: NPI.

Payload Hash (optional).

Populated if you have a current "truth".

Blank if buyer has no knowledge and is asking for most recent.

Format Validation Result Transaction id (Optional).

Populated if current "truth" has been validated by Open APIs and result persisted to Public BC.

Fulfillment Request Type.

Potential Types: Update to Truth, Data Quality Issue Notification, New Data Asset.

Contains PHI.

Contains PM.

Contains PCI.

API URL to access data Payload.

Only allows one access for a validator to Pull information for validation purposes.

Validator API Secret(s).

Encrypted Value using Validator Public Key, Validator then decrypts to gain API access to the data asset.

Buyer API Secret(s).

Encrypted Value using Buyer Public Key, Buyer then decrypts to gain API access to the data asset.

Expire Time.

Note that each write to the Blockchain would require a transaction fee and that fee would be paid to the infrastructure (miner) who was determined the leader by the consensus mechanism for the network at that point in time.

3) Validator verifies contract is fulfilled:

Validator can GET open validation requests that they have access to validate.

This flags the Record as being validated for a specific time to reduce wasted validation effort.

Validator uses their Private key to decrypt the pass phrase and uses this to access the Sellers API endpoint to fetch the data asset.

After fetching the data asset the validator verifies the Buyers Requirements.

If Successful the Validator exercises the Smart Contract to write to the block chain and mark the Buy Request as Fulfilled.

The smart contract would:

Return the escrow to the Seller, if applicable;

Increase the Sellers Credibility score for the specifics of this data asset including metrics like specific data field updated, geographic information, type of data Provider Data, source/channel, Owner;

Transfer funds from the Buyer to the Seller for the Fulfilling the Buy request, these funds may be escrowed for some warranty period;

Transfer funds from the Buyer to the Validator for Validating the Sellers Data Asset, these funds may be escrowed for some warranty period.

The Buyer would then have access to the Sellers API to fetch the data Asset via using their private key to decrypt the pass phrase and use the result to access the Sellers API endpoint to fetch the data asset.

The Validator ensures the Buyers receives the data asset by either pushing the asset to the Buyers API endpoint or making the data asset available at a mutually agreed upon API endpoint for a predetermined period of time.

If Unsuccessful the validator exercises the Smart Contract to write to the block chain and mark the Buy request as Unfulfilled.

The Smart Contract would:

Use the Sellers escrow to the Pay the Validation Cost;

Decrease the Sellers Credibility score for the specifics of this data asset including metrics like specific data field updated, geographic information, type of data Provider Data, source/channel, Owner;

Allow the validator to fulfill the contract if the true information was learned in the process of validation for the same fee;

Inform the seller of details around why the validation failed;

The status of contract would remain unfulfilled and open to sellers to fulfill.

Each write to the Blockchain would require a transaction fee and that fee would be paid to the infrastructure (miner) who was determined the leader by the consensus mechanism for the network at that point in time.

In the above embodiment, the seller encrypts the validator's API "key" with the validator's public key and shares that when requesting to fulfill the buy order. This would ensure only the validator can decrypt the API key using their (the validator's) private key.

Once decrypted the validator can use the key that is now decrypted to access the API and fetch the seller's data asset. Others on the network would not be able to utilize the API URL or the encrypted key to access the seller's data asset.

As discussed above, in one embodiment, a smart contract is written as a piece of computer code into the Blockchain platform. The smart contract contains logic and serves as the mechanism to write to the ledger. The ledger of the present invention keeps track of debits and credits for each participant. In addition to the exchange of funds the ledger will also store meta data about the data asset (e.g., hash of the data, type, format, API URL, etc.) to inform the network what specifically was exchanged. The ledger will also hold information to infer creditability of the participants for each of the transactions. If an exchange was unsatisfactory, the participants have a way to note that to ensure the network is aware. A triggering event, as discussed in the example above (e.g., seller posts data asset and the asset is validated), is met and the smart contract executes according to the coded terms and instructions.

FIGS. 7-12 illustrates example ledger formats of one embodiment of the present invention. FIG. 7 illustrates one embodiment of a ledger for the present invention. FIG. 8 illustrates one embodiment of a buy order block stored on the ledger of FIG. 7. FIG. 9 illustrates one embodiment of an open API validation block stored on the ledger of FIG. 7. FIG. 10 illustrates one embodiment of a seller fulfillment request block stored on the ledger of FIG. 7. FIG. 11 illustrates one embodiment of a fulfilment request validation block stored on the ledger of FIG. 7. FIG. 12 illustrates one embodiment of a fund transfer block stored on the ledger of FIG. 7.

In one embodiment, the present invention would run on private or permissioned chain. Buyer, sellers, and validators access to the Blockchain can be as a client or as a node of the Blockchain. In one embodiment, the buyers and sellers access the Blockchain via a node that is connected to network of nodes participating. The buyers and sellers can also run a node and participate as one of the nodes on the Blockchain's peer to peer network. Users can run a node and their clients would access the Blockchain (ledger and smart contracts) via their node(s).

In the preferred embodiment, the smart contract would execute with in the Blockchain Technology Stack. Each node would agree on the output of that transaction given inputs and the logic defined in the smart contract.

The system of the present invention leverages Blockchain technologies like a "library card catalog" and allow other systems to reference that data in a secure yet open way. The data is anchored to the Blockchain by persisting a representative hash of the data and a URL of where to find it that is only available to the entities that can decrypt the "secret" (e.g., password) that was encrypted by the seller with the target firm(s) public keys. The configuration of smart contracts according to the present invention enables an open data marketplace that connects buyers and sellers to exchange data assets and validate requirements are met in an automated or process via the validator actor.

In one embodiment, the hash and URL are written to the ledger. The smart contract is the logic executed by the seller to take the inputs and write that data as outputs for all to see in the shared distributed ledger. Since the ledger is "public" and, because access to the data for that URL should be limited to the buyer of the data, a "secret" or encrypted value is provided that only the buyer can decrypt and use to access the data payload. This allows the reference information to live in plain sight, however when the buyer/validator system attempts access, it will decrypt the "secret" that was encrypted using the public key the buyer provided in the smart contract. This ensures that others do not access the data because they would not be able to decrypt the secret to obtain the API access key. The hash is stored on the ledger for all to see to ensure transparency so all participants know that the data has not changed. For instance, that hash would ensure that the seller did not attempt to fulfill the order for data without having the data. The data must match that hash or the validation process fails. Others on the network would also have the ability to compare their inventory of data assets to what has been proposed. For example Seller2 may have a data asset that the Buyer is requesting and if the hash of Seller2's data matched the hash provided by Seller1's proposed fulfillment request then Seller2 knows that Seller1 has proposed the same data. However, if Seller2 notices that Seller1 has different data they would have a couple of new options. Option1 is that they could buy from Seller1 and update their inventory, option2 would be to propose a competing offer to meet the buyer's request, which would indicate Seller2 believes Seller1 has lower quality data. The buyer's validation process would then make the decision on which Seller met the requirements and received payment.

Blockchains are open so private data should not be stored in it. Because even if the data is encrypted at some point, that encryption may be susceptible to be broken. Using Blockchain as the reference point enables the existing silos to be more connected. Users can efficiently connect to one distributed data marketplace instead of directly connecting to a plurality of "trusted" silos directly in a very inefficient mechanism. Discovery can then occur on the marketplace so buyers and sellers can connect, however the data asset inventory would still be held in the silo and transferred once the requirements were met using APIs and existing technologies. Blockchain helps connect the disparate systems so buyers and sellers can connect via the market instead of directly which is now very limited and expensive.

The use of smart contracts, as configured according to the present invention, create an open and transparent way for buyers and sellers to trust the marketplace because of its transparency. This allows for an industry utility or even a potentially autonomous solution that is supported solely by the network of buyers and sellers that utilize it versus a corporate entity that is trying to make profit from it.

While certain embodiments of the present invention are described in detail above, the scope of the invention is not to be considered limited by such disclosure, and modifications are possible without departing from the spirit of the invention as evidenced by the following claims:

What is claimed is:

1. A system for maintaining data sets by way of a blockchain platform, the system comprising:

one or more non-transitory computer readable mediums comprising software code, which when executed, configures one or more processors to:

publish open, open, standing requests on the blockchain platform from a buyer user for updates to a data set for improved accuracy and for accuracy validations of the updates proposed to the data set;

establish a smart contract on the blockchain platform designating a first reward for fulfilling the open, standing request for the updates and a second reward for fulfilling the open, standing request for the accuracy validations;

receive a first responsive submission on the blockchain platform from a first user regarding a proposed update to the data set which corrects one or more errors in the data set, said first submission including an encrypted value comprising, in encrypted form, a pointer to a data resource located off the blockchain platform storing the proposed update, at least the encrypted value of said first submission being encrypted using a public key of the first user and the first submission being signed using a private key of the first user;

receive a second responsive submission on the blockchain platform from a second user regarding an accuracy validation submission for the proposed update, said second submission being encrypted by a public key of the second user and signed using a private key of the second user;

authorize payment of the first reward to the first user and payment of the second reward to the second user following receipt of both the first submission from the first user and the second submission from the second user indicating an accurate, validated update to the data set; and receive and decrypt the encrypted value from the first submission from the first user using the private key of the first user to locate the validated update to the data set for access using the pointer, in decrypted form.

2. The system of claim 1 wherein:

the one or more non-transitory computer readable mediums store software code, which when executed, configures the one or more processors to electronically disburse the first reward and the second reward by way of the blockchain platform from an account associated with an entity providing the smart contract.

3. The system of claim 2 wherein:

the submission from the first user includes an address for an account associated with the first user for funds; and the one or more non-transitory computer readable mediums store software code, which when executed, configures the one or more processors to authorize, by way of the blockchain platform, escrow of the payment for the second reward after receiving the submission from the first user and prior to receiving the submission from the second user, wherein the escrowed payment of the second reward is provided from the account associated with the first user in accordance with the address.

4. The system of claim 3 wherein:

the one or more non-transitory computer readable mediums store software code, which when executed, configures the one or more processors to authorize, by way of the blockchain platform, a payment at least totaling the first reward and the second reward from the account associated with the entity providing the smart contract to the account associated with the first user in accordance with the address.

5. The system of claim 1 wherein:

the pointer comprises, when decrypted, a URL pointer to the data resource, accessible by way of a web service and application program interface.

6. The system of claim 1 wherein:

the encrypted value comprises, in encrypted form, a password for accessing the data resource; and the one or more non-transitory computer readable mediums store software code, which when executed, configures the one or more processors to use the password, in decrypted form, to access the data resource.

7. The system of claim 1 wherein:

the one or more non-transitory computer readable mediums store software code, which when executed, configures the one or more processors to store the data set as a one-way cryptographic hash of data.

8. The system of claim 1 wherein:

the data set comprises a collection of medical data.

9. The system of claim 1 wherein:

the data set, the submission from the first user, and the submission from the second user are stored on a ledger of the blockchain platform.

10. The system of claim 1 wherein:

the one or more non-transitory computer readable mediums store software code, which when executed, configures the one or more processors to receive, at the blockchain platform, one or more public keys for acceptable validators, including the second user.

11. The system of claim 1 wherein:

the one or more non-transitory computer readable mediums store software code, which when executed, configures the one or more processors to publish, on the blockchain platform, a trusted data set for comparison against the data set for accuracy.

12. The system of claim 1 wherein:

the one or more non-transitory computer readable mediums store software code, which when executed, configures the one or more processors to, after each of providing the data set, receiving the submission from the first user, receiving the submission from the second user, authorizing the payment of the first reward, and authorizing the payment of the second reward, authorizing a respective mining payment to a respective mining user associated with the blockchain platform.

13. A computer-implemented method for maintaining data sets by way of a blockchain platform, the method comprising:

publishing public, open, standing requests on the blockchain platform from a buyer user for updates to a data set for improved accuracy and for accuracy validations of the updates proposed to the data set;

establishing a smart contract on the blockchain platform designating a first reward for fulfilling the open, standing request for the updates and a second reward for fulfilling the open, standing request for the accuracy validations;

receiving a first responsive submission on the blockchain platform from a first user regarding a proposed update to the data set which corrects one or more errors in the data set, said first submission including an encrypted value comprising, in encrypted form, a pointer to a data resource located off the blockchain platform storing the proposed update, at least the encrypted value of said first submission being encrypted using a public key of the first user and the first submission being signed using a private key of the first user;

receiving a second responsive submission from a second user on the blockchain platform regarding an accuracy validation submission for the proposed update, said second submission being encrypted by a public key of the second user and signed using a private key of the second user;

authorizing payment of the first reward to the first user and payment of the second reward to the second user following receipt of both the first submission from the first user and the second submission from the second user indicating an accurate, validated update to the data set; and receiving and decrypting the encrypted value from the first submission from the first user using the private key of the first user to locate the validated update to the data set for access using the pointer, in decrypted form.

* * * * *